United States Patent
Jouvin

(10) Patent No.: US 6,641,296 B1
(45) Date of Patent: Nov. 4, 2003

(54) METHOD FOR MIXING ALGINATE USING A ROTATABLE ELLIPTICAL BOWL

(76) Inventor: Jean-Luc Jouvin, 11 Rue de la Perle, 72000 Le Mans (FR)

( * ) Notice: Subject to any disclaimer, the term of this patent is extended or adjusted under 35 U.S.C. 154(b) by 0 days.

(21) Appl. No.: 09/442,730

(22) Filed: Oct. 22, 1999

Related U.S. Application Data

(63) Continuation of application No. PCT/FR98/00833, filed on Apr. 24, 1998.

(30) Foreign Application Priority Data

Apr. 24, 1997 (FR) .............................................. 97 05091

(51) Int. Cl.⁷ ................................................. B01F 15/02
(52) U.S. Cl. .................................. 366/173.2; 366/175.3
(58) Field of Search ........................ 366/34, 40, 53–59, 366/65, 92–95, 130, 219, 165.1–165.5, 166.1, 167.1, 173.1, 173.2, 175.1, 181.6, 182.4, 602, 175.3

(56) References Cited

U.S. PATENT DOCUMENTS

| | | | |
|---|---|---|---|
| 926,144 A | * 6/1909 | Sherow | |
| 1,025,206 A | * 5/1912 | Rounds | |
| 1,157,092 A | * 10/1915 | Du Rell | |
| 1,241,518 A | * 10/1917 | Jaeger | |
| 1,313,395 A | * 8/1919 | Lenz | |
| 1,789,320 A | * 1/1931 | Overbury | |
| 2,126,911 A | * 8/1938 | Mullen | |
| 2,192,806 A | * 3/1940 | Smith | |
| 2,306,962 A | * 12/1942 | Kropp | |
| 2,851,942 A | * 9/1958 | Ashenden, Jr. | |
| 2,861,787 A | * 11/1958 | Csanyi | |
| 2,917,395 A | * 12/1959 | Csanyi | |
| 3,134,579 A | * 5/1964 | Booth, Sr. | |
| 3,214,145 A | * 10/1965 | Brown, Jr. | |
| 3,277,540 A | * 10/1966 | Buhrer | |
| 3,291,304 A | * 12/1966 | Fuchs | |
| 3,304,063 A | * 2/1967 | Ranson | |
| 3,610,586 A | * 10/1971 | Price et al. | |
| 3,647,397 A | * 3/1972 | Coleman | |
| 3,751,011 A | * 8/1973 | Milik | |
| 3,778,033 A | 12/1973 | Pullman | |
| 3,802,822 A | * 4/1974 | Harbison | |
| 3,820,763 A | * 6/1974 | Questi, Sr. et al. | |
| 4,041,648 A | * 8/1977 | Heiberger | |
| 4,057,223 A | * 11/1977 | Rosenberger | |
| 4,182,683 A | * 1/1980 | Irvine et al. | |
| 4,212,546 A | * 7/1980 | Porteous | |
| 4,443,111 A | * 4/1984 | Minaire | |
| 4,506,984 A | * 3/1985 | Strehlow | 366/65 |
| 4,531,673 A | * 7/1985 | Holland et al. | |
| 5,052,554 A | * 10/1991 | Leonard | |
| 5,121,990 A | * 6/1992 | Guiet et al. | 366/602 |
| 5,352,037 A | * 10/1994 | Jouvin | |
| 5,618,105 A | * 4/1997 | Baker | |
| 5,702,181 A | * 12/1997 | Wright | 366/40 |
| 5,709,467 A | * 1/1998 | Galliano, II | |
| 6,042,259 A | * 3/2000 | Hines et al. | 366/34 |
| 6,109,778 A | * 8/2000 | Wilmer | |
| 6,116,772 A | * 9/2000 | DiGiacomo et al. | |

FOREIGN PATENT DOCUMENTS

| | | |
|---|---|---|
| DE | 72 13 810 | 8/1972 |
| DE | 195 11 245 | 10/1995 |
| FR | 2718058 | * 10/1995 |
| GB | 1 282 956 | 7/1972 |
| GB | 1 367 354 | 9/1974 |
| WO | 98/47607 | * 10/1998 |

* cited by examiner

Primary Examiner—Charles E. Cooley
(74) Attorney, Agent, or Firm—Young & Thompson

(57) ABSTRACT

A mixer for alginate has a rotatable bowl and one or more nozzles positioned above the opening of the rotatable bowl for injecting water into the bowl. By controlling the injection of water at appropriate locations and at appropriate strengths (i.e., pressures and rates), desired mixing of the alginate can be achieved.

6 Claims, 2 Drawing Sheets

METHOD FOR MIXING ALGINATE USING A ROTATABLE ELLIPTICAL BOWL

CROSS-REFERENCE TO RELATED APPLICATIONS

This is a continuation of PCT application serial number PCT/FR98/00833, filed on Apr. 24, 1998, which claims priority from French patent application serial number 97/05091, filed on Apr. 24, 1997.

BACKGROUND OF THE INVENTION

1. Field of the Invention

The present invention relates to the field involving the preparation of alginate by mixing.

2. Description of the Related Art

Alginate is a product used in dentistry. This product comes in the form of a powder to which is added a defined amount of water in order to obtain the consistency of a paste. Prior to use, the dentist implements preparation of the required amount in a mixer that homogenizes the preparation. Known in the state of the art is the French patent filed as No. 9403702, and issued as French Patent No. 2,718,058 A1. This patent describes a mixer that provides for the injection of water into the bowls via nozzles.

It was seen that the presence of water wetting the bottom of the bowl ensured very high quality mixing without any need for premixing. The mixing time was decreased in a very significant manner and it was possible to mix up to 4 doses per bowl without the risk of leaving powder packed at the bottom of the bowl.

SUMMARY OF THE INVENTION

The object of the present invention is to improve the mixer according to the state of the art.

For this purpose, the invention pertains first of all to a mixer comprising means for the injection of water into the bowls via one or more nozzles, preferably 4 nozzles. In the cases in which the bowls lack a center part, more nozzles are required to wet this central part.

In one embodiment the present invention is a mixer for the preparation of alginate comprising (a) a rotatable bowl rotatable about an axis of rotation and having an elliptical opening for receiving the alginate and defined by a large axis greater than a small axis; and (b) one or more nozzles positioned above the opening of the rotatable bowl for injecting water into the bowl such that the alginate is mixed solely by the injection of the water as the bowl rotates about the axis of rotation with respect to the one or more nozzles.

In another embodiment, the present invention is a method for preparing alginate, comprising the steps of (a) placing the alginate into a mixer comprising (1) a rotatable bowl rotatable about an axis of rotation and having an elliptical opening for receiving the alginate and defined by a large axis greater than a small axis; and (2) one or more nozzles positioned above the opening of the rotatable bowl for injecting water into the bowl; and (b) injecting the water into the bowl while the bowl is rotating such that the alginate is mixed solely by the injection of the water as the bowl rotates about the axis of rotation with respect to the one or more nozzles.

In according with one embodiment of the present invention, the nozzles comprise one or more stainless steel tubes of a length of circa 20 mm and a diameter on the order of 1.3 mm.

In accordance with a preferred embodiment of the present invention, the nozzles are fed via a pressure valve that controls the pressure.

Advantageously, the pressure of the water jets is between 2 and 4 bar.

In accordance with a preferred embodiment of the present invention, the mixer comprises a calculator for defining the amount of water injected in relation to the number of doses of alginate introduced into the bowl.

BRIEF DESCRIPTION OF THE DRAWINGS

Better comprehension of the invention will be provided by the description below with reference to the attached drawings corresponding to a nonlimitative example of implementation in which.

DETAILED DESCRIPTION

Figure 1:
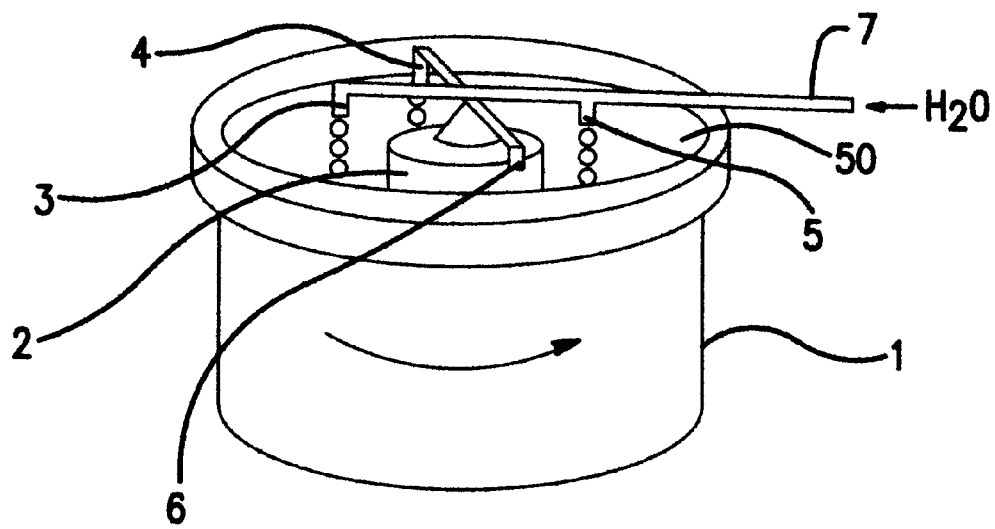
FIG. 1 represents a perspective view of the bowl.
Figure 3:
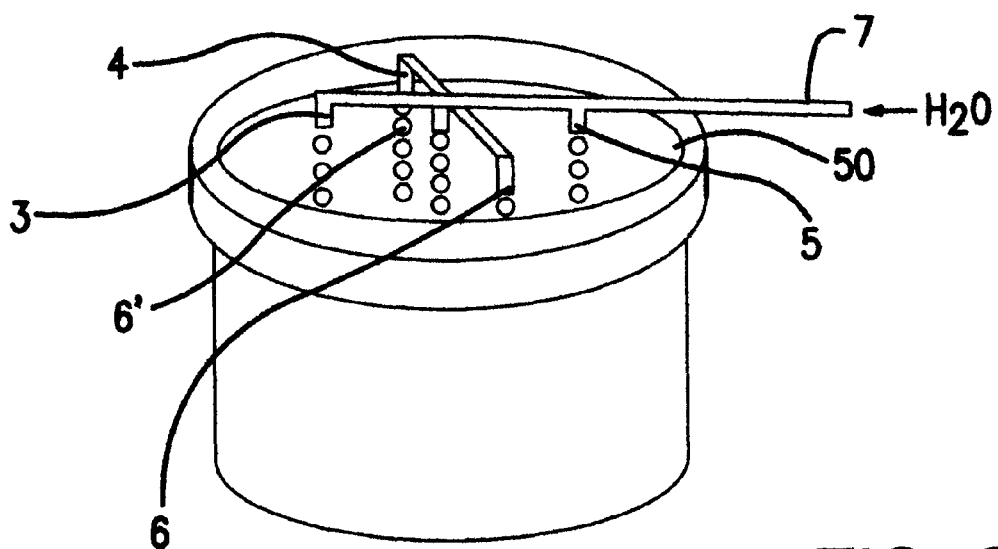
FIG. 3 represents a perspective view of the bowl without a center part and further including a fifth nozzle.
Figure 4:
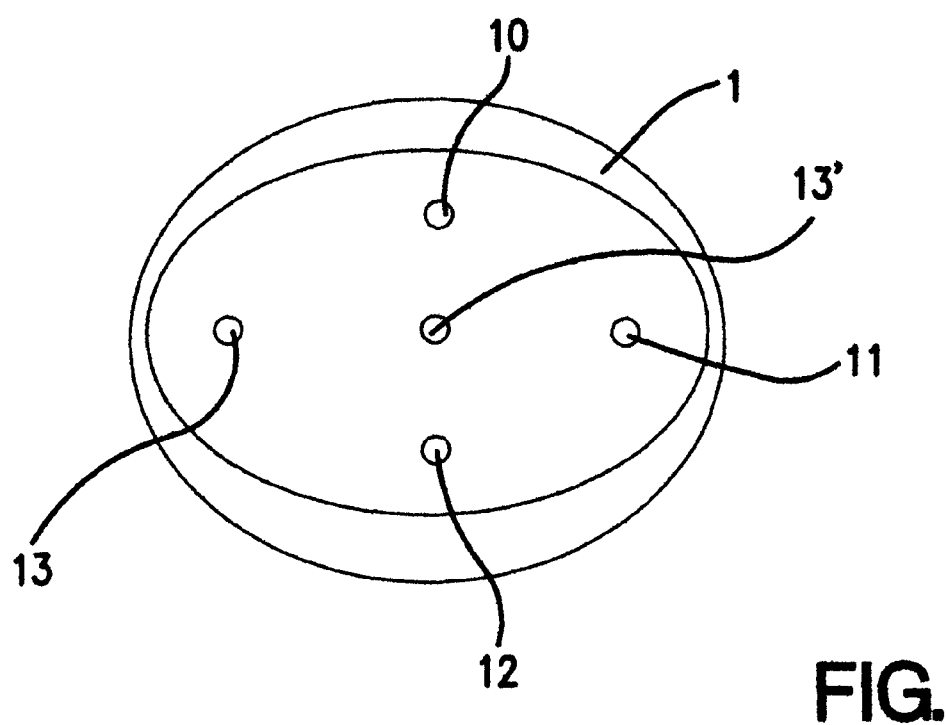
FIG. 4 represents a plan view of the mixer bowl of FIG. 3.

FIG. 1 represents a perspective view of one type of rotatable bowl (1) with a central hub (2) and elliptical opening 50. The mixer has 4 nozzles (3 to 6) fed by a common conduit (7). FIG. 3 illustrates an embodiment in which the bowl has no center part, and a fifth nozzle 6' is added to wet the central part of the bowl at injection point 13' (FIG. 4). The nozzles (3 to 6) are diametrically opposite each other and spaced apart by circa 50 mm, along the large axis of an ellipse, and circa 36 mm along its small axis, such that the nozzles can traverse the powder and wet the bottom of the bowl at four equidistant points located at the same distance from the internal and external edges.

Figure 2:
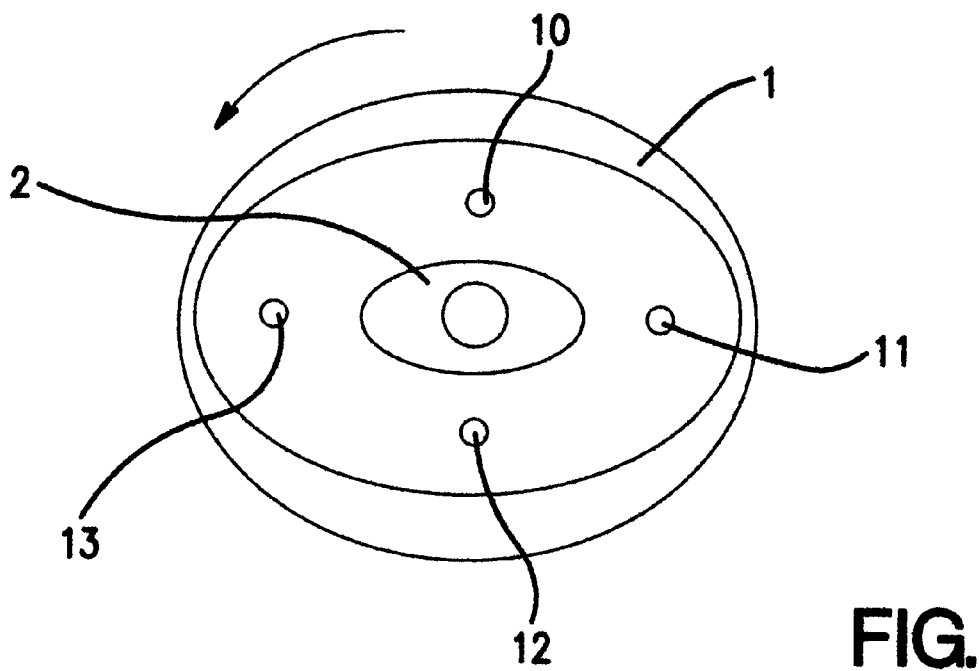
FIG. 2 represents a plan view of the mixer bowl.

As illustrated in FIG. 2, the hub has an elliptical shape defined by a large axis greater than a small axis, the large and small axes of the hub being aligned with the large and small axes of the opening. The first and third nozzles define a first line through the axis of rotation, and the second and fourth nozzles define a second line through the axis of rotation, orthogonal to the first line, as illustrated in FIGS. 1 and 2.

The nozzles (3 to 6) are made out of small stainless steel tubes of variable length, but preferably ca. 20 mm in length. Their inside diameter is also variable but the diameter of 13/10 mm yields excellent results.

The water pressure should be between 0 and 8 bar, preferably between 2 and 4 bar, so as to be able to penetrate the powder and reach the bottom of the bowl. In fact, the speed and quality of the mixing is essentially dependent on the wetting of the bottom of the bowl.

The stability of the injection is ensured by a pressure valve set between 0 and 8 bar, preferably between 2 and 4 bar. The injection of water must be performed in a continuous manner; pumps providing intermittent flow are not suitable because even when two are placed in phase opposition there is always a splashing phenomenon linked to the intermittent flow which sprays powder in the air and soils the machine, especially the nozzles.

The amount of water injected into each bowl is selected in advance on the basis of the number of doses; it is entered into the memory by the microprocessor which retains the same number of doses until it is changed. Calibration is implemented when the machine is installed at a given site.

The installed software allows upward or downward adjustment of the number of ml per dose; this change can be for one specific use or entered in the memory.

FIG. 2 shows a plan view of the bowl (1) after injection of the water. The surface of the powder exhibits injection points (10 to 13).

In a preferred embodiment of the present system, the mixer comprises a calibration system controlled by the microprocessor based on the control of the injection time so as to adapt to the water distribution networks; it includes autonomous systems with pressure.

The invention has been described above as a nonlimitative example. It is obvious that an expert in the art could implement variants of implementation without, however, going beyond the scope of the invention.

What is claimed is:

1. A method for preparing alginate from alginate in powder form, the method comprising the successive steps of:

providing a mixing bowl containing alginate powder;

injecting water into the bowl via at least four nozzles distributed above an opening of the bowl, the water being injected of a continued manner and at a sufficient pressure, to cause the water to penetrate the powder and reach the bottom of the bowl; and mixing the powder and the injected water in the bowl.

2. The method according to claim 1, in which the nozzles are paired opposite one another with respect to the bowl's axis.

3. The method according to claim 1, said bowl having no central part, in which the water is also injected in the center of the bowl via a fifth nozzle.

4. The method according to claim 1, in which the amount of injected water is calculated based on a number of doses of the alginate powder provided in the bowl.

5. The method according to claim 1, wherein an injection time is controlled by a calibration system to adapt to a water distribution network that supplies the injected water.

6. The method according to claim 1, in which the injection pressure is between 2 and 4 bars.

* * * * *